(12) United States Patent
Butler et al.

(10) Patent No.: US 9,789,259 B2
(45) Date of Patent: Oct. 17, 2017

(54) INJECTION DEVICE WITH DOSE SETTING MECHANISM HAVING MAXIMUM DOSE STOP

(75) Inventors: Joseph Butler, Warwickshire (DE); David Martin Leak, Lake Hopatcong, NJ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/994,628

(22) PCT Filed: Dec. 16, 2011

(86) PCT No.: PCT/EP2011/073078
§ 371 (c)(1),
(2), (4) Date: Jun. 14, 2013

(87) PCT Pub. No.: WO2012/084720
PCT Pub. Date: Jun. 28, 2012

(65) Prior Publication Data
US 2013/0267911 A1    Oct. 10, 2013

(30) Foreign Application Priority Data
Dec. 21, 2010  (EP) .................................... 10196230

(51) Int. Cl.
*A61M 5/315*    (2006.01)
*A61M 5/24*     (2006.01)

(52) U.S. Cl.
CPC .... *A61M 5/31551* (2013.01); *A61M 5/31585* (2013.01); *A61M 5/24* (2013.01); *A61M 5/31541* (2013.01); *A61M 5/31561* (2013.01); *A61M 5/31568* (2013.01); *A61M 2205/581* (2013.01); *A61M 2205/582* (2013.01)

(58) Field of Classification Search
CPC .............. A61M 5/315; A61M 5/31501; A61M 5/31528; A61M 5/31533; A61M 5/3155; A61M 5/31551; A61M 5/31541; A61M 5/31561; A61M 2005/3154
USPC ................................ 604/207, 208, 211, 224
See application file for complete search history.

(56) References Cited

U.S. PATENT DOCUMENTS

| 6,003,736 A | 12/1999 | Ljunggren |
| 7,427,275 B2 * | 9/2008 | DeRuntz et al. ............. 604/207 |
| 8,226,631 B2 | 7/2012 | Boyd et al. |

(Continued)

FOREIGN PATENT DOCUMENTS

| CN | 1780652 A | 5/2006 |
| DE | 202008011175 U1 | 1/2010 |

(Continued)

OTHER PUBLICATIONS

Form PCT/IB/326, Notification Concerning Transmittal of International Preliminary Report on Patentability.

(Continued)

*Primary Examiner* — Nathan R Price
*Assistant Examiner* — Weng Lee
(74) *Attorney, Agent, or Firm* — McDonnell Boehnen Hulbert & Berghoff LLP

(57) ABSTRACT

A dose setting mechanism for a drug delivery device is provided comprising a dose setting member and a further element. Maximum dose stop features are provided on a housing and on the further element.

6 Claims, 1 Drawing Sheet

(56) References Cited

U.S. PATENT DOCUMENTS

| | | | |
|---|---|---|---|
| 2006/0030838 A1 | 2/2006 | Gonnelli | |
| 2007/0093761 A1* | 4/2007 | Veasey | A61M 5/31546 |
| | | | 604/207 |
| 2007/0123829 A1* | 5/2007 | Atterbury et al. | 604/207 |
| 2009/0264828 A1 | 10/2009 | Dette et al. | |
| 2010/0094253 A1* | 4/2010 | Boyd et al. | 604/506 |
| 2010/0274198 A1 | 10/2010 | Bechtold | |
| 2014/0316349 A1 | 10/2014 | Veasey et al. | |

FOREIGN PATENT DOCUMENTS

| | | |
|---|---|---|
| EP | 1603611 B1 | 5/2008 |
| EP | 1923084 A1 | 5/2008 |
| EP | 2193816 A1 | 6/2010 |
| WO | 0154757 A1 | 8/2001 |
| WO | 2004030730 A2 | 4/2004 |
| WO | 2006089767 A1 | 8/2006 |
| WO | 2010097125 A1 | 9/2010 |
| WO | 2010139668 A1 | 12/2010 |

OTHER PUBLICATIONS

Form PCT/IPEA/416, Notification of Transmittal of the International Preliminary Report on Patentability.
English Translation of Notice of Reason(s) for Rejection issued in Japanese Patent Application No. 2013-545222 dated Oct. 20, 2015.
English Translation of First Office Action Issued in Chinese Patent Application No. 201280014504.8 dated Dec. 15, 2014.

\* cited by examiner

INJECTION DEVICE WITH DOSE SETTING MECHANISM HAVING MAXIMUM DOSE STOP

CROSS REFERENCE TO RELATED APPLICATIONS

The present application is a U.S. National Phase Application pursuant to 35 U.S.C. §371 of International Application No. PCT/EP2011/073078 filed Dec. 16, 2011, which claims priority to European Patent Application No. 10196230.6 filed Dec. 21, 2010. The entire disclosure contents of these applications are herewith incorporated by reference into the present application.

FIELD OF INVENTION

The present invention is directed to a dose setting mechanism for a drug delivery device, like a pen-type injector, that provides for administration by injection of a medicament from a multidose cartridge.

BACKGROUND

EP 1 603 611 B1 discloses an injector where a user may set the dose. The principal assembly of a drug delivery device and its drive mechanism are disclosed in EP 1 603 611 B1, to which reference is made for further details. Such injectors have application where regular injection by persons without formal medical training occurs. This is increasingly common amongst those having diabetes where self-treatment enables such persons to conduct effective management of their diabetes. These circumstances set a number of requirements for pen-type injectors of this kind.

The injector must be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be cheap to manufacture and easy to dispose of (preferably being suitable for recycling).

In the manufacture of such medical devices there are often advantages in producing a family of products based on a common device platform. For example, simplification of manufacturing processes or reductions in costs of tools are such advantages.

In addition, in some cases the settable maximum dose of the drug delivery device may not be appropriate for each of the drugs to be delivered. One example may be long acting insulin and short acting insulin. Another example may be to prevent children using such a drug delivery device from setting a too high dose.

Thus, there is a need for providing a reliable mechanism allowing choosing the appropriate maximum settable dose in a drug delivery device platform with a minimum of effort for changes compared to a standard device and a minimum of replacement parts.

In WO 01/54757 A1 a dose setting limiter is described having a first part formed as a dose setting dial and fitted over a rotary dose setting knob of the medical injector. The maximal allowable dose is preselected with the dose setting limiter disconnected from the housing of the medical injector by rotating a further part until a marker on said further part is placed over a desired maximal allowable dose indication on a scale. When dialling the first part clockwise a protrusion provided on the first part will abut another protrusion located on the further part once the preselected desired dose is reached, thereby preventing larger doses from being set. All movements during setting of a dose are rotational movements without axial components of the movements. Thus, the maximum distance a user may move the dose setting knob is limited to about 360° which either makes the maximum distance small or increases the overall dimensions of the device.

Further, WO 2006/089767 A1 discloses a dose setting mechanism comprising a dose setting member and a housing. The dose setting member is provided with a first stopping member which is permanently rotationally coupled to the dose setting member and may be adjusted in its axial position relative to the dose setting member. In addition, the housing is provided with a second stopping member which abuts the first stopping member if a preset maximum dose has been set such that a further dose can not be set.

In WO 2010/097125 A1 a dose setting mechanism comprising a tubular distal housing with threads on its inner surface is described, with said threads cooperating with a first thread segment on the outer circumference surface of a tubular dose limiting member. A tubular dose setting member is coaxially arranged inside the dose limiting member. A removable lock member is attached to the distal housing and comprises one elongated rib on its inner circumferential surface to interact with a protrusion of the dose limiting member in order to lock the dose limiting member in a certain position in a presetting phase. During dose setting a stop surface of the tubular dose limiting member interacts with an end surface of an outer thread of the dose setting member to limit the set dose.

SUMMARY

It is an object of the present invention to provide an improved dose setting mechanism allowing for the maximum dose of a drug delivery device (injection device) to be modified.

This is obtained by a dose setting mechanism as defined in claim 1. A dose setting mechanism according to the present invention comprises a housing, a dose setting member which is movable relative to the housing to set a dose and a further element which is at least partially located within the housing and which is moved in a first axial direction relative to the housing during dose setting. Preferably the housing and the further element are provided with corresponding stop means which are arranged to limit the movement of the further element in the first axial direction during dose setting thereby defining a maximum settable dose. In other words, direct contact or abutment of stop means provided on or within the housing on the one hand and corresponding stop means provided on or in the further element on the other hand prevent further axial movement of the further element relative to the housing during dose setting, which in turn obviates setting a higher dose. Thus, the position of the stop means may be chosen as required to pre-select the maximum settable dose of the dose setting mechanism.

The further element may be any member of a dose setting mechanism which performs an axial movement relative to the housing during dose setting. Preferably, the further element performs an axial movement relative to the housing during dose dispensing, too. An axial movement may either be a straight translational displacement or a translational component of a movement along an e.g. helical path. In a dose setting mechanism several components, such as e.g. a display member (number sleeve), drive member (drive sleeve), a nut member, a clicker member, a clutch member, a rotation prevention member, a spring member, a unidirectional coupling, or the like, may perform an axial movement relative to the housing during dose setting. With respect to the present invention, at least one of such components is provided with a stop means.

The dose setting member is typically the element a user has to handle to dial a dose. Thus, the dose setting member may be provided e.g. in the form of a knob or a grip. In addition, the dose setting member may comprise further means for displaying the set dose, e.g. in the form of a number sleeve indicating in a window a digit corresponding to the number of units dialled.

According to a preferred embodiment of the present invention the stop means comprise a protrusion or a recess formed on the further element and corresponding stop element formed on the housing. As the further element is at least partially located within the housing, the protrusion or recess may be formed on the outer face of the further element and the corresponding stop element may be formed on the inner face of an e.g. tubular housing.

Preferably, the movement of the further element during dose setting is a translational displacement in the first axial direction. According to the present invention a translational displacement includes only an axial component of the movement, i.e. no additional rotational movement, e.g. on a helical path. The further element might be a spring-like or washer-like element having at least one external protrusion which is guided in the corresponding axial groove on the housing with the length of the groove defining the maximum settable dose. If the dose setting mechanism or the drug delivery device is designed similar to that shown in EP 1 603 611 B1, such a spring-like or washer-like element may be disposed on a tubular drive sleeve and between a flange of this drive sleeve and a front face of a clutch means with the further element biasing the clutch means towards a position coupling the dose dial sleeve and the drive sleeve for setting a dose. The dose dial sleeve and the drive sleeve may be decoupled by pushing a knob or button which action leads to a compression of the spring-like or washer-like element.

According to an alternative embodiment of the present invention the movement of the further element during those setting is a movement along a helical path having a rotatory component and a translational component in the first axial direction. The stop element of the housing might be provided as a first protrusion located on the inner face of the housing and the further element might be a sleeve-like element, e.g. a drive sleeve as described in EP 1 603 611 B1, with a second protrusion being provided on this further element. The distance between the first and second protrusions defines the maximum settable dose. In other words, a variation of one or both of the stop means allows preselecting the maximum settable dose. Even if the movement during dose setting may comprise a rotatory component, the stop means act due to an abutment in the axial direction.

It is preferred to design the dose setting mechanism such that the dose setting member and the further element are coupled during dose setting such that the dose setting member and the further element move in unison. Preferably, this synchronised movement is a rotation of the dose setting member and the further element. However, a relative axial movement between the dose setting member and the further element might be possible e.g. if the dose setting member and the further element move along helical paths having a different pitch.

It is further preferred if the dose setting member and the further element are decoupled during dose dispensing such that the dose setting member is e.g. free to rotate relative to the further element. In other words, while the dose setting member may be moved back along a helical path during dose dispensing the further element might be pushed in an axial direction without a rotatory component of the movement. In the decoupled state of the dose setting member and the further element a relative axial movement between these two components might be allowed, too.

Preferably the dose setting mechanism further comprises a piston rod for dose dispensing. This piston rod might be guided within the housing and might act on a piston located in a cartridge for dose dispensing. According to the present invention the piston rod is not in direct contact with the dose setting member. For example the further element, which might be a drive sleeve, is interposed between the dose setting member and the piston rod.

In addition, the piston rod and the dose setting member might be decoupled during dose dispensing such that the dose setting member and the piston rod move relative to each other during dose dispensing. This relative movement might include a rotatory component with the piston rod and the dose setting member rotating at different rotational speeds and/or the relative movement might include a translational component with the piston rod and the dose setting member moving with different speed in an axial direction or in a different axial direction.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

BRIEF DESCRIPTION OF THE DRAWINGS

In the following, the invention will be described by a way of examples and with reference to the schematic drawings in which.

DETAILED DESCRIPTION

Hereinafter, the features of the present invention are described with reference to the drug delivery device shown in FIG. 1 which is similar to the device disclosed in EP 1 603 611 B1.

Although the present invention is described with reference to this specific drug delivery device, the dose setting mechanism may be applicable to other variable dose injection devices, where the maximum dose is limited in a similar manner. In other words, it may equally be applied to any drug delivery device where the maximum dose stop is determined by features of two separate components moving towards one another and making contact when the maximum dose is reached. This could apply both to rotationally moving components, e.g. in a diallable variable dose pen, or axially travelling components, e.g. in a pull-push fixed dose pen. Furthermore, the present invention is described with respect to disposable drug delivery devices, but is applicable also for reusable drug delivery devices.

Figure 1:
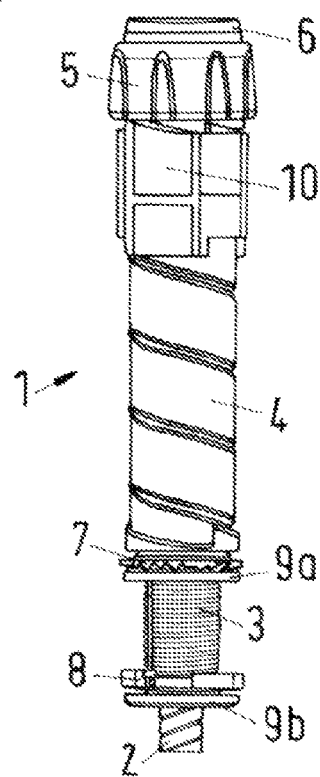
FIG. 1 shows a dose setting mechanism similar to that disclosed in EP 1 603 611 B1.

The drive mechanism 1 shown in FIG. 1 comprises a housing (not shown). A cartridge (reservoir), containing medicinal product, can be mounted to the housing and retained by any suitable means. The cartridge and its retaining means are not shown in FIG. 1. The cartridge may contain a number of doses of a medicinal product and also typically contains a displaceable piston. Displacement of the piston causes the medicinal product to be expelled from the cartridge via a needle (also not shown). The housing or an insert fixed within the housing is provided with a threaded circular opening. A helical thread extends along the inner cylindrical surface of the housing.

The drive mechanism 1 further comprises a piston rod 2, a drive sleeve 3, a dose dial sleeve 4 with a dose knob 5, a button 6, a spring member 7, a nut 8 and a clutch means (not shown). The spring member 7 is provided between a flange 9a formed on the drive sleeve 3 and a front face of the clutch means. The housing or a separate window part 10 may be provided with an internal helical thread engaging the external surface of the dose dial sleeve 4.

The piston rod 2 is of generally circular section. One end of the piston rod is provided with a first thread which is engaged with the thread or formed in the circular opening of the housing or its insert. On the upper end in FIG. 1 the piston rod 2 is provided with a second thread which engages an internal thread formed within the tubular drive sleeve 3. The first thread and the second thread are oppositely disposed and may have a different pitch.

The drive sleeve 3 extends about the piston rod 2. The drive sleeve is generally cylindrical with two flanges 9a, 9b provided on its lower end in FIG. 1. The two flanges 9a, 9b are spaced a distance along their drive sleeve with an external helical thread provided on the outer part of the drive sleeve between the two flanges. The nut is located between the drive sleeve and the housing and disposed between the two flanges of the drive sleeve. The nut 8 can be either a half-nut or a full-nut. The nut has an internal thread that is engaged with the external thread of the drive sleeve 3. The outer surface of the nut 8 and an internal surface of the housing are keyed together by means of longitudinally directed splines to prevent relative rotation between the nut 8 and the housing, while allowing relative longitudinal movement there between.

The spring member 7 is disposed about the drive sleeve 3 on the side facing away from the nut 8 of the upper flange 9a in FIG. 1. The metal spring 7 may be formed as an undulated or a bent washer. The outer surface of the spring 7 and an internal surface of the housing are keyed together by means of longitudinally directed splines to prevent relative rotation between the spring 7 and the housing, while allowing relative longitudinal movement there between.

The clutch means (not shown) may be designed as a sleeve which is disposed about the drive sleeve 3 within the dose dial sleeve 4. The clutch means may have means for engaging the spring 7 on its lower side in FIG. 1 and means for engaging dose dial sleeve 4 and/or dose knob 5 on its upper side in FIG. 1. Such means for engaging the further components of the dose setting mechanism can include corresponding teeth. Spring 7 biases the clutch means into engagement with the dose dial sleeve 4 and/or dose knob 5. Further, the clutch means and the drive sleeve 3 may be keyed together such that the drive sleeve 3 follows a rotation of the clutch means while allowing relative longitudinal movement there between. The engagement between the spring 7 and the clutch means is preferably designed such that the clutch means may perform a relative rotational movement with respect to spring 7 if the clutch means is in engagement with the dose dial sleeve 4 or dose knob 5.

The dose knob 5 is designed as a dose dial grip which is fixed to the dose dial sleeve 4. The dose knob 5 has a grippable surface allowing a user to dial a dose by rotating the dose knob 5 which thus forms a dose setting member. The dose dial sleeve 4 and the dose knob 5 both have a central opening on the upper side in FIG. 1 to receive a pin of button 6 which acts on the clutch means allowing to push the clutch means towards flange 9a of the drive sleeve against the force of spring 7.

Operation of the drive mechanism in accordance with the mechanism shown in FIG. 1 will now be described.

To dial a dose, a user rotates the dose knob 5. The spring member 7 applies an axial force to the clutch means in the upwards direction in FIG. 1. The force exerted by the spring 7 couples the clutch means to the dose knob 5 for rotation. As the dose knob 5 is rotated, the associated dose dial sleeve 4, the drive sleeve 3 and the clutch means all rotate in unison.

Audible and tactile feedback of the dose being dialled is provided by the spring 7 and the clutch means. The spring 7 cannot rotate with respect to the housing, so the spring deforms allowing the teeth or the like of the clutch means to jump over the e.g. teethed spring 7 producing an audible and tactile 'click'.

The helical thread of the dose dial sleeve 4 and the internal helical thread of the drive sleeve 3 have the same lead. This allows the dose dial sleeve 4 to advance along the thread of the housing or its insert 10 at the same rate as the drive sleeve 3 advances along the thread of the piston rod 2. Rotation of the piston rod 2 is prevented due to the opposing direction of the threads of the piston rod 2. The further thread of the piston rod 2 is engaged with the thread of the housing or its insert and so the piston rod 2 does not move with respect to the housing while a dose is dialed.

The nut 8, keyed to the housing, is advanced along the external thread of the drive sleeve 3 by the rotation of the drive sleeve 3. When a user has dialed a quantity of medicinal product that is equivalent to the deliverable volume of the cartridge, the nut 8 reaches a position where it abuts the upper flange 9a of the drive sleeve 3. A radial stop formed on the surface of the nut 8 contacts a radial stop on the surface of the flange 9a of the drive sleeve 3, preventing both the nut 8 and the drive sleeve 3 from being rotated further.

Should a user inadvertently dial a quantity greater than the desired dosage, the drive mechanism 1 allows the dosage to be corrected without dispense of medicinal product from the cartridge. The dose knob 5 is counter-rotated. This causes the system to act in reverse.

When the desired dose has been dialled, the user may then dispense this dose by depressing the button 6 in the direction of the first end (lower end in FIG. 1) of the drive mechanism 1. The button 6 applies pressure to the clutch means, displacing same axially with respect to the dose knob 5. This causes the clutch means to disengage from the dose knob 5. However, the clutch means remains keyed in rotation to the drive sleeve 3. The dose knob 5 and associated dose dial sleeve 4 are now free to rotate (guided by the helical thread of the housing).

The axial movement of the clutch means deforms the spring member 7 and couples e.g. the teeth at the lower end of the clutch means to the spring 7 preventing relative rotation there between. This prevents the drive sleeve 3 from rotating with respect to the housing, though it is still free to move axially with respect thereto.

Pressure applied to the button 6 thus causes the dose knob 5 and the associated dose dial sleeve 4 to rotate into the housing. Under this pressure the clutch means, the spring 7 and the drive sleeve 3 are moved axially in the direction of the lower end of the drive mechanism 1 in FIG. 1, but they do not rotate. The axial movement of the drive sleeve 3 causes the piston rod 2 to rotate though the threaded opening in the housing or its insert, thereby to advance the piston within the cartridge, causing the medicinal product to be expelled from the cartridge. The selected dose is fully delivered as the dose knob 5 returns to a position where it abuts the housing.

When pressure is removed from the button 6, the deformation of the spring member 7 is used to urge the clutch means back along the drive sleeve 3 to re-couple the clutch means with the dose knob 5. The drive mechanism is thus reset in preparation to dial a subsequent dose.

Figure 2:
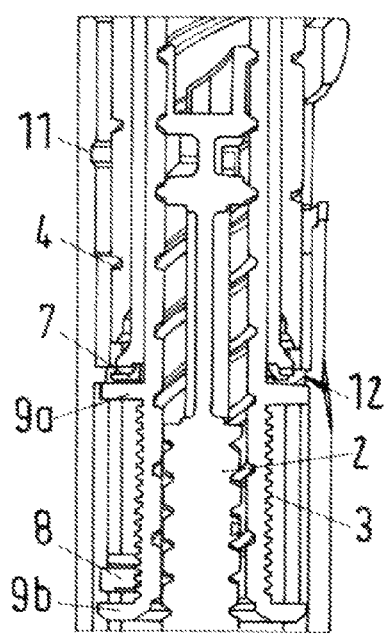
FIG. 2 shows a sectional view of the dose setting mechanism according to a first embodiment of the invention and FIG. 3 shows a sectional view of the dose setting mechanism of a second embodiment of the invention.

A first embodiment of the invention is shown in the sectional view of FIG. 2 with the components described above with respect to FIG. 1 essentially corresponding to those shown in FIG. 2. Thus, same reference numerals are used to denominate identical parts. In FIG. 2 a tubular housing 11 is shown surrounding dose dial sleeve 4 and drive sleeve 3.

On the inner side of the tubular housing 11, a flange-like protrusion 12 is provided forming a first stop means for limiting the axial movement of drive sleeve 3 within the housing 11. The protrusion 12 is designed such that the flange 9a of the drive sleeve abuts flange 12 if the drive sleeve 3 is moved in the upwards direction of FIG. 2 during dose setting. In other words, the user may dial a dose as described above with respect to FIG. 1 which causes the drive sleeve 3 to be moved along a helical path defined by the threads on the piston rod 2 and the corresponding threads within drive sleeve 3. However, the distance the drive sleeve 3 is allowed to travel during this dialling movement is limited by flange 12 of the housing 11. As dialling a dose is limited by flange 12, the position of flange 12 relative to flange 9a of the drive sleeve 3 defines the maximum settable dose of the dose setting mechanism 1.

The position of flange 12 and/or the position of flange 9a of the drive sleeve 3 may be varied to preselect a different maximum settable dose for the dose setting mechanism 1.

As an alternative to the embodiment shown in FIG. 2, further elements of the drive sleeve 3 may be used as a stop means for abutting flange 12 to define a maximum settable dose.

Figure 3:
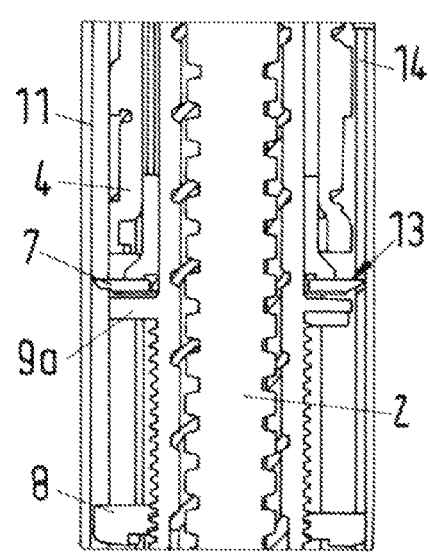

A second embodiment of the present invention is shown in FIG. 3 which again generally corresponds to the dose setting mechanism shown in FIG. 1. The embodiment shown in FIG. 3 differs from the embodiment of FIG. 2 in that no additional flange 12 is provided on the inner side of the housing 11 thus allowing drive sleeve 3 to move freely within housing 11.

As mentioned above with respect to FIG. 1 spring 7 and the internal surface of the housing 11 are keyed together by means of longitudinally directed splines to prevent a relative rotation between spring 7 and the housing 11 while allowing relative longitudinal movement there between. In the embodiment shown in FIG. 3 said splines comprise a protrusion 13 formed on the outer surface of spring 7 and a longitudinal groove 14 formed on the internal surface of housing 11. The length of groove 14 is limited, thus allowing only a limited longitudinal movement of spring 7 relative to housing 11. In other words, protrusion 13 and groove 14 form corresponding stop means which limit the movement of the dose setting mechanism during dose dialling. Hence, the length of groove 14 defines a maximum settable dose of the dose setting mechanism 1.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dose setting mechanism for a drug delivery device, the mechanism comprising:
   a housing comprising an internal helical thread,
   a dose setting member comprising an external surface that engages the internal helical thread of the housing such that the dose setting member is movable relative to the housing to set a dose,
   a drive sleeve which is at least partially located within the housing and which is moved along a helical path having a rotatory component and a translational component in a first axial direction relative to the housing during dose setting,
   a threaded piston rod in threaded engagement with the drive sleeve,
   wherein an inner side of the housing and a proximal flange of the drive sleeve define corresponding stops,
   wherein the corresponding stops are arranged to abut one another so as to limit the movement of the drive sleeve in the first axial direction during dose setting thereby defining a maximum settable dose, and wherein
   the dose setting member and the drive sleeve are decoupled during dose dispensing such that the dose setting member is free to rotate relative to the drive sleeve and
   the piston rod is free to rotate relative to the drive sleeve.

2. The dose setting mechanism according to claim 1, wherein the housing has a first protrusion and the drive sleeve has a second protrusion and wherein the distance between the first and second protrusions defines the maximum settable dose.

3. The dose setting mechanism according to claim 1, wherein the dose setting member and the drive sleeve are coupled during dose setting and wherein the dose setting member and the drive sleeve are rotated together during dose setting.

4. The dose setting mechanism according to claim 1, wherein the piston rod is in direct contact with the drive sleeve.

5. The dose setting mechanism according to claim 1, wherein the dose setting member and the piston rod are decoupled during dose dispensing such that the dose setting member and the piston rod are allowed to move relative to each other during dose dispensing.

6. The dose setting mechanism according to claim 1, further comprising a reservoir containing a medicament, preferably insulin, which reservoir is attached to the housing.

* * * * *